United States Patent
Sterzer

Patent Number: 5,386,837
Date of Patent: Feb. 7, 1995

[54] METHOD FOR ENHANCING DELIVERY OF CHEMOTHERAPY EMPLOYING HIGH-FREQUENCY FORCE FIELDS

[75] Inventor: Fred Sterzer, Lawrence Township, Mercer County, N.J.

[73] Assignee: MMTC, Inc., Princeton, N.J.

[21] Appl. No.: 11,817

[22] Filed: Feb. 1, 1993

[51] Int. Cl.6 .............................. A61B 19/00
[52] U.S. Cl. ................................. 128/898
[58] Field of Search ............... 600/2; 607/2, 3, 154, 607/901, 58, 72–74, 148; 128/898, 24.1, 24 AA, 630; 606/32

[56] References Cited

U.S. PATENT DOCUMENTS

| | | | |
|---|---|---|---|
| 4,528,265 | 7/1985 | Becker | 435/172.1 |
| 4,558,690 | 12/1985 | Joyce | 128/804 |
| 4,665,898 | 5/1987 | Costa et al. | 128/804 |
| 4,671,254 | 6/1987 | Fair | 128/804 |
| 4,800,899 | 1/1989 | Elliott | 128/804 |

OTHER PUBLICATIONS

"Electrochemotherapy, a new antitumor treatment" Belehradek et al, Abstract.
"Local and Systematic Antitumor Effects in Mice of the Combination of Electrochemotherapy and an Immunotherapy" Mir et al, Abstract.

Primary Examiner—William E. Kamm
Assistant Examiner—Marianne Parker
Attorney, Agent, or Firm—George J. Seligsohn

[57] ABSTRACT

Pulse shocks of high-frequency wave energy (e.g. RF, microwave, high-energy infra-red or laser electromagnetic wave energy or ultrasonic acoustic wave energy), rather than DC electric pulses, are employed to non-invasively produce force fields of an intensity sufficient to create transient pores in the plasma membranes of targeted cells, such as tumor cells or other diseased cells, through which either locally or systemically applied drug or chemotherapeutic agents can easily enter and be taken up by the targeted cells, even for (1) the cells of a deep-seated tumor, (2) non-localized metastasized tumor cells within a patient's body, or (3) cells (e.g., blood cells) temporarily removed to outside of a patient's body.

14 Claims, 5 Drawing Sheets

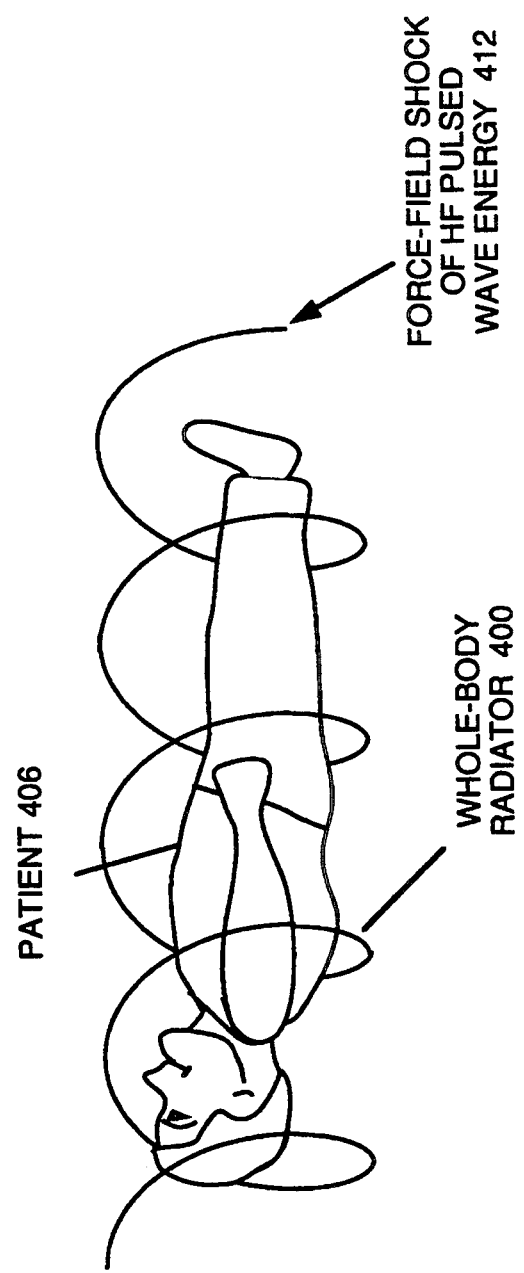

METHOD FOR ENHANCING DELIVERY OF CHEMOTHERAPY EMPLOYING HIGH-FREQUENCY FORCE FIELDS

BACKGROUND OF THE INVENTION

1. Field of the Invention

The present invention relates to the use of force fields to enhance the absorption of a chemotherapeutic agent, comprising one or more particular drugs, by targeted cells and, more particularly, the use of high-frequency force fields for this purpose.

2. Description of the Prior Art

As known in the art for some time, standard chemotherapy as a treatment for a tumor or cancer, AIDS or certain other diseases involves the use of a drug (or drugs) to which particular target cells are significantly more sensitive than are normal cells. For instance, in the case of a tumor or cancer, such drugs are more effective in poisoning tumor cells than they are in poisoning normal cells, and in the case of Graves disease radioactive iodine is targeted to thyroid cells for the purpose of destroying some of them. While in some cases the chemotherapeutic drug may be applied directly to the cells of the tumor or other targeted cells themselves, usually such a drug is applied systemically. Standard chemotherapy maintains the concentration of systemically-applied drugs in the blood and other exta-cellular body fluids at a relatively low level in order to limit any damage to normal cells. However, this results in the maximum amount of the chemotherapeutic drug that is actually taken up and delivered into a targeted cell by passing through its cell plasma membrane also being limited to a lower level than would otherwise be optimum.

Recently, a new electrochemotherapy [ECT] antitumor treatment has been developed, which treatment consists of locally delivering shocks of high-intensity DC electrical pulses to tumor sites a short time after the systemic administration of chemotherapy. The DC electrical pulses open large transient pores in the plasma membranes of the exposed cells. The chemotherapeutic agents can enter the cells through these pores resulting in locally enhanced cytotoxicity. More specifically, it is believed that each high-intensity electrical DC pulse shock produces a sufficiently high force field across the plasma membrane of each of the exposed cells to cause the plasma membrane to break down and puncture in response thereto, thereby creating the aforesaid pores in the exposed cells.

ECT using DC pulses has been successfully used in conjunction with bleomycin, a cytotoxic compound which causes DNA breaks and cleaves some RNA. A few hundred bleomycin molecules in the cell cytosol are sufficient to induce cell death. In vitro experiments have shown that using 10% cell survival as a criterion, cells subjected to ECT are 650,000 times more sensitive to bleomycin than those exposed to bleomycin alone. In the case of mice with spontaneous breast tumors, the amount of bleomycin required for remission was so small that the drug if given alone was ineffective and did not seem to induce any secondary effects. Highly encouraging trial results were obtained in patients with head and neck tumors using 4 or 8 DC pulses with amplitudes of 1300 volts/cm and duration of 100 microseconds ($\mu$s). The pulses were delivered by means of metallic electrodes placed on the skin on either side of the malignant nodules.

A problem is that the implementation of ECT with shocks of DC pulses and non-invasive electrodes is limited to the treatment of small cutaneous tumor lesions, since it would be very difficult to non-invasively produce the required DC electric force field strength in subcutaneous or deep-seated tumors. The present invention is directed to a solution of this problem which permits the required strength of a force field to be conveniently produced even in the cells of deep-seated tumors or other types of targeted cells using one or more non-invasive applicators.

SUMMARY OF THE INVENTION

In accordance with the principles of the present invention, pulse shocks of high-frequency wave energy (e.g. RF, microwave, high-energy infra-red or laser electromagnetic wave energy or ultrasonic acoustic wave energy), rather than DC electric pulses, are employed to non-invasively produce, with minimal or, if desired, a controlled amount of temperature rise in a patient's body tissues, force fields of an intensity sufficient to create transient pores in the plasma membranes of targeted cells, such as tumor or other diseased cells, through which chemotherapeutic agents can easily be delivered, enter and taken up by these targeted cells, even for (1) deep-seated cells (e.g., the cells of a deep-seated tumor) or (2) non-localized diseased cells (e.g., metastasized tumor cells) within a patient's body.

BRIEF DESCRIPTION OF THE DRAWING

FIG. 4 illustrates the application of force-field shock pulses to the whole body of a patient for enhancing delivery of a systemically administered chemotherapeutic agent into metastasized tumor cells in the body of the patient.

DESCRIPTION OF THE PREFERRED EMBODIMENTS

Figure 1:
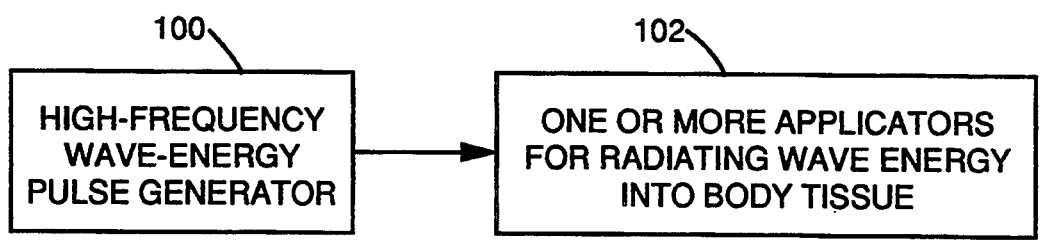
FIG. 1 is a generalized block diagram of equipment used to conveniently apply one or more high-frequency wave-energy force-field pulses of the required strength to any of various types of targeted cells within a patient's body.

Referring to FIG. 1, there is shown in general terms the type of equipment required to perform the electrochemotherapeutic method of the present invention. As shown, a train of one or more pulses of high-frequency (HF) wave energy from high-frequency wave-energy pulse generator 100 are applied to each of one or more applicators 102 for radiating wave energy into body tissue of a patient. Depending on particular use, the HF wave energy may comprise RF, microwave, high-energy infra-red or laser electromagnetic wave energy or, alternatively, ultrasonic acoustic wave energy. In any case, the frequency of the wave energy radiated by each of applicators 102 is such as to be able to penetrate to a lesser or greater extent into body tissue. Further, in the case in which there are more than one applicators 102, corresponding pulses of wave energy radiated therefrom may, for reasons to be discussed below, be relatively time delayed with respect to one another.

It is essential in performing the electrochemotherapeutic method of the present invention that the peak power of the pulsed wave energy irradiating targeted cells, which are to be treated, of the patient's body be sufficiently high to produce force-field shocks to the plasma membranes of these cells that cause their plasma membranes to break down and puncture in response thereto, thereby creating pores in these plasma membranes, through which a systemically administered chemotherapeutic agent may easily enter and be taken up. Further, it is often desirable that the average power of the pulsed wave energy producing these force-field shocks be sufficiently low as to effect only a minimal rise in the temperature of all irradiated cells of the patient's body. By way of an example, the peak power of the pulsed wave energy may be 10 kW, while the average power of the pulsed wave energy may be only 100 mW, (i.e., a pulsed-wave-energy duty cycle of only 0.001 percent) However, in some cases, it is therapeutically desirable that the average power of the pulsed wave energy be sufficient to raise the temperature of all irradiated cells of the patient's body by a controlled amount while the force-field shocks are being produced. For instance, the uptake and/or efficacy of a drug or chemotherapeutic agent that is delivered into a targeted cell may be greater at a certain controlled elevated temperature. Also, the use of high-frequency force-field ECT, forming the subject of the present invention, may be beneficially used in conjunction with other treatment modalities (such as hyperthermia or X-rays, by way of examples).

Figure 2:
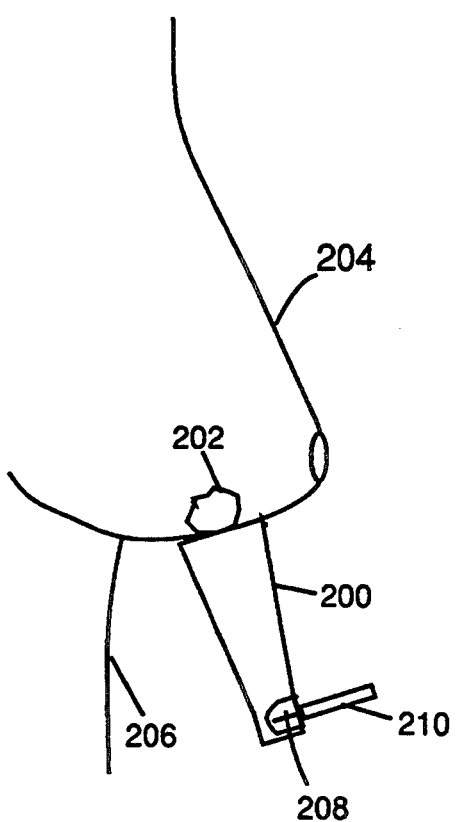
FIG. 2 shows an illustrative example of the application of force-field shock pulses to a localized, relatively superficially-seated breast tumor lesion of a patient for enhancing delivery of a systemically administered chemotherapeutic agent into the cells of the superficially-seated breast tumor lesion.

Referring to FIG. 2, there is shown an illustrative example of an applicator comprising a single ceramic horn antenna 200 for non-invasively applying a highly directional beam of force-field shock of HF pulsed wave energy into the cells of a superficially-seated tumor lesion 202 in breast 204 of patient 206 from outside of the patient's body without any substantial application of this directional beam to the normal tissue of patient 206. It is assumed that force-field shock of HF pulsed wave energy is applied to superficially-seated breast tumor lesion 202 a short time after the systemic administration of a chemotherapeutic agent to patient 206; that the intensity of force-field shock of HF pulsed wave energy is sufficient to cause the plasma membranes of the cells of superficially-seated tumor lesion 202 to break down and puncture in response thereto, thereby creating pores in these plasma membranes through which the systemically administered chemotherapeutic agent may easily enter; and that the duty cycle of the pulses of force-field shock of HF pulsed wave energy is sufficiently low as to either effect only a minimal rise in the temperature of all the cells of superficially-seated tumor lesion 202 or a controlled rise of such temperature.

For illustrative purposes, the applicator is shown in FIG. 2 as a single ceramic horn antenna 200 having a radiating element 208 to which pulses of microwave energy (which may have a frequency of about 915 MHz) are applied from a microwave pulse generator (not shown) through coaxial cable 210. However, it should be understood that the the applicator for non-invasively applying a highly directional beam of force-field shock of HF pulsed wave energy into the cells of superficially-seated tumor lesion 202 may take other forms known in the art. For instance, the applicator could comprise an array of two or more capacitor plates, rather than comprising ceramic horn antenna 200.

Figure 3B:
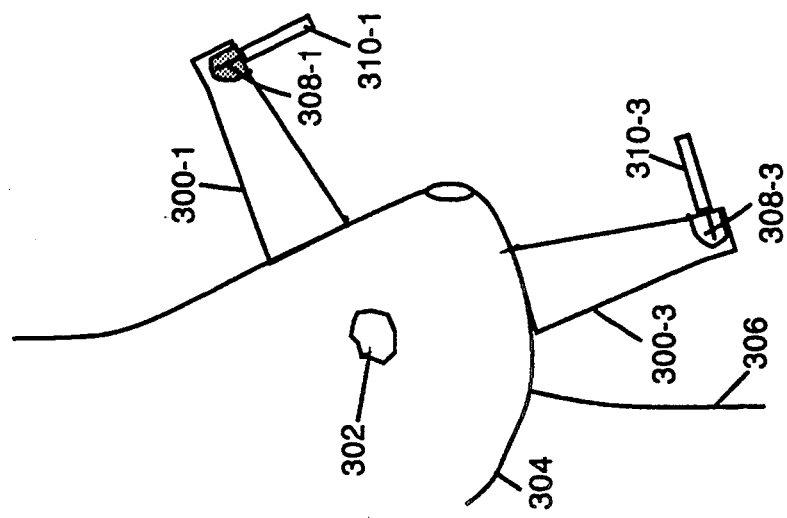
FIG. 3a (front view) and 3b (side view) together show an illustrative example of the application of force-field shock pulses to a localized, relatively deep-seated breast tumor lesion of a patient for enhancing delivery of a systemically administered chemotherapeutic agent into the cells of the deep-seated breast tumor lesion.
Figure 3A:
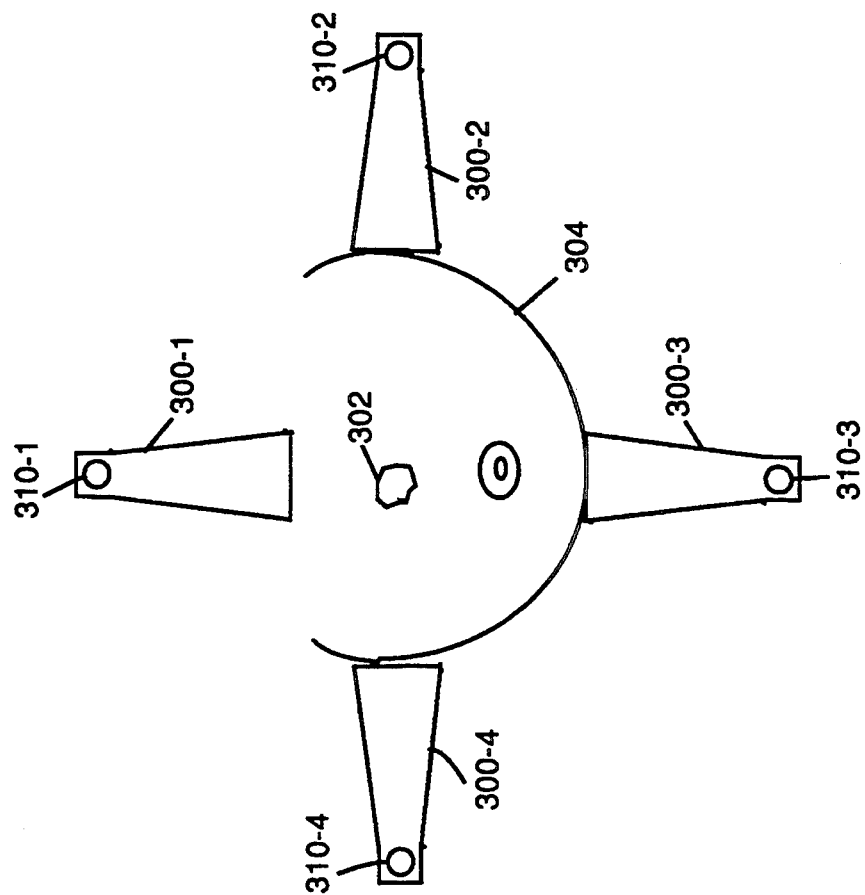

Referring to FIGS. 3a (front view) and 3b (side view), there is shown an illustrative example of an applicator for non-invasively applying a highly directional beam of force-field shock of HF pulsed wave energy into the cells of a deep-seated tumor lesion 302 in breast 304 of patient 306 from outside of the patient3 s body without any substantial application of this directional beam to the normal tissue of the patient. The applicator shown in FIGS. 3a and 3b comprises the four ceramic horn antennas 300-1, 300-2, 300-3 and 300-4, each of which is similar to above-described ceramic horn antenna 200. Specifically, ceramic horn antennas 300-1, 300-2, 300-3 and 300-4, respectively, include radiating elements 308-1, 308-2, 308-3 and 308-4 (only radiating elements 308-1 and 308-3 being visible in the drawing) to which pulses of microwave energy (which may have a frequency of about 915 MHz) are synchronously applied from a microwave pulse generator (not shown) through respective coaxial cables 310-1, 310-2, 310-3 and 310-4. The four ceramic horn antennas 300-1, 300-2, 300-3 and 300-4, each of which is angularly spaced about 90° from its adjacent ceramic horn antennas, surround breast 304 on the outside of the patient. Each of four ceramic horn antennas 300-1, 300-2, 300-3 and 300-4 is positioned to radiate a highly directional beam of force-field shock of HF pulsed wave energy into the site of the cells of deep-seated breast tumor lesion 302. The relative timing of corresponding pulses of HF wave energy radiated by each of four ceramic horn antennas 300-1, 300-2, 300-3 and 300-4 (which, depending upon the particular location of breast tumor lesion 302 in breast 304, may be concurrent or may be suitably time-delayed with respect to one another by the microwave pulse generator) is such that the respective intensities thereof combine within the site of deep-seated breast tumor lesion 302.

Unlike the highly directional beam of force-field shock of HF pulsed wave energy radiated by ceramic horn antenna 200, described above, the intensity of force-field shock of HF pulsed wave energy radiated by each of ceramic horn antennas 300-1, 300-2, 300-3 and 300-4 is insufficient in itself to cause the plasma membranes of the cells of deep-seated breast tumor lesion 302 to break down and puncture in response thereto or to cause any significant damage to the normal cells of breast 304 through which it passes. However, the combined intensity within the site of deep-seated breast tumor lesion 302 of all four highly directional beams of force-field shock of HF pulsed wave energy is sufficient to cause the plasma membranes of the cells of deep-seated breast tumor lesion 302 to break down and puncture in response thereto, thereby creating pores in these plasma membranes through which the systemically administered chemotherapeutic agent may easily enter and be taken up by the cells of deep-seated breast tumor lesion 302.

The principles exemplified by FIGS. 3a and 3b is not limited to treating deep-sighted breast tumors by the particular arrangement shown in FIGS. 3a and 3b, but can be extended to any type of applicator comprising a plurality of two or more radiators each of which may non-invasively apply a highly directional beam of force-field shock of HF pulsed wave energy to the site of a deep-seated tumor lesion (or the site of other deep-seated tissue of a patient to be treated by ECT) from different positions outside of the body of the patient., wherein the radiated intensity from each of the plurality radiators is insufficient to cause significant damage to normal cells but the combined intensity thereof is sufficient to provide ECT treatment within the site. The use of such a plurality of directional applicators is particularly suitable for treating large deep-seated tumors. For instance, a deep-seated tumor lesion within the torso of a patient may be treated by two large ceramic horn antennas or a capacitor array comprising plates situated on opposite sides of a patient's body. In this case, lower (e.g., 27 or 40 MHz) RF frequency wave energy would be employed to provide a sufficient tissue penetration capability.

In those cases in which the cells of certain types of metastasized tumors are poisoned to a much greater extent by a certain concentration of a particular chemotherapeutic agent than are normal cells, the ECT treatment method of the present invention may be used to advantage. More specifically, as schematically illustrated in FIG. 4 by whole-body radiator 400, the cells of the whole body (or at least a substantial portion of his whole body) of patient 406 is irradiated by force-field shock of HF pulsed wave energy 412, which has a sufficient intensity to cause the plasma membranes of both of metastasized tumor and normal cells of the body of patient 406 to break down, puncture, and create pores therein through which the particular chemotherapeutic agent may easily enter and be taken up. The result is that the concentration of the systemically administered particular chemotherapeutic agent needed to poison the metastasized tumors is significantly lowered. While more of the lower concentrated particular chemotherapeutic agent enters the patient's normal cells, the damage to these normal cells is limited by the fact that the cells of the metastasized tumors are poisoned to a much greater extent by the lower concentration of the particular chemotherapeutic agent than are normal cells. While FIG. 4 shows whole-body radiator 400 as a coil, it may comprise a capacitor array or some other form instead.

Reference is now made to U.S. Pat. No. 5,007,437, which issued to me on Apr. 16, 1991 and is assigned to the same assignee as the present application. U.S. Pat. No. 5,007,437 teaches the use of a balloon catheter for the treatment of prostate cancer and/or benign prostatic hypertrophy (BPH) by heating the prostate of a patient with continuous-wave (cw) microwaves applied to a microwave antenna of the balloon catheter and radiated from this microwave antenna to compressed prostate tissue through compressed non-prostate tissue surrounding an orifice (e.g., the urethra or rectum) of the patient in the vicinity of his prostate, while the balloon catheter is inflated. This compression increases the therapeutic temperature to which the prostate tissue more distal to the microwave antenna can be heated without heating any non-prostate tissue beyond a maximum safe temperature, and reduces the temperature differential between the heated more distal and more proximate prostate tissue from the microwave antenna.

Figure 5:
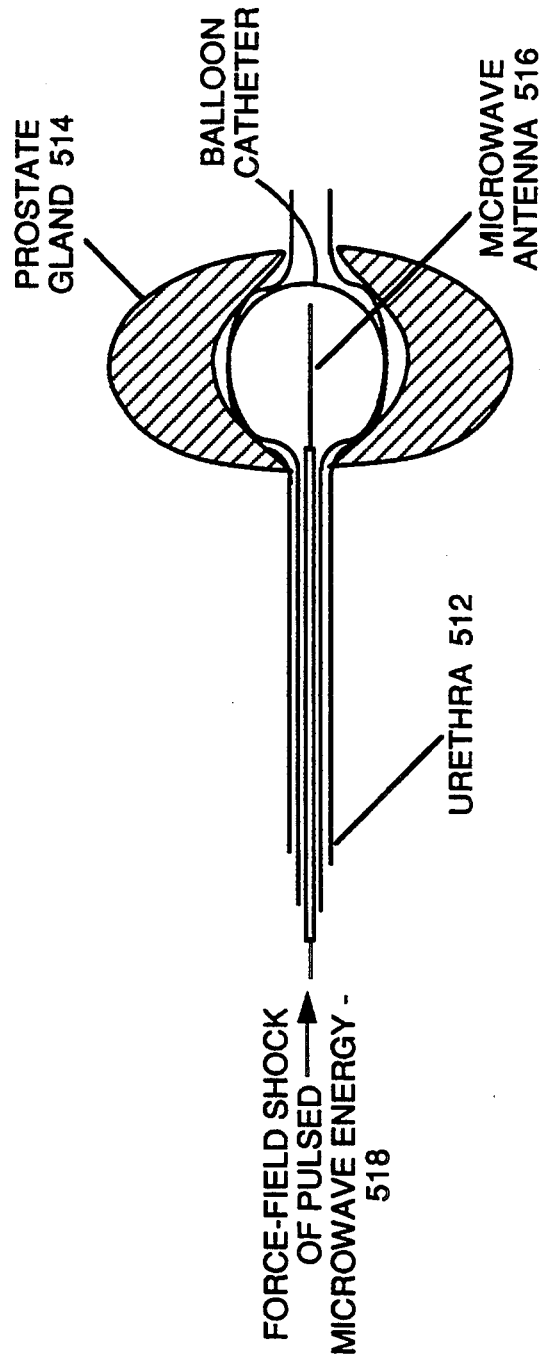
FIG. 5 shows a preferred way in which microwave wave-energy force-field pulses can be applied to the prostate gland of a patient for the purpose of enhancing delivery of a systemically administered chemotherapeutic agent into cells thereof.

FIG. 5 schematically shows a species of the balloon catheter disclosed in U.S. Pat. No. 5,007,437 in which inflated balloon catheter 510, inserted in urethra 512 of a patient, compresses his prostate gland 514, while prostate gland 514 is irradiated from microwave antenna 516. However, in the case of FIG. 5, microwave antenna 516 is energized by a force-field shock of pulsed microwave energy 518, rather than by continuous-wave (cw) microwave energy (as is the case taught in U.S. Pat. No. 5,007,437). Further, in the case of FIG. 5, the energy in each pulse of the pulsed microwave energy and the duty cycle of the pulsed microwave energy are sufficiently low to effect only a minimal rise in the temperature of the prostate and non-prostate tissue, or, in some cases, a controlled rise to a temperature which enhances the uptake and efficacy of a systemically applied drug. This differs from the case taught in U.S. Pat. No. 5,007,437 wherein the purpose of the applied cw microwave energy is to heat the prostate all the way up to a relatively high therapeutic temperature which is still below a safe temperature for non-prostate tissue through which the microwave energy penetrates.

In FIG. 5, compression of prostate gland 514 by the use of inflated balloon catheter 510 makes it possible to increase the intensity of the force-field shock of pulsed microwave energy applied to microwave antenna 516 so that the irradiated intensity thereof at the more distal prostate cells is sufficient to cause the plasma membranes of these cells to break down, puncture, and create pores therein, while the differential in irradiated intensity between that at the more distal prostate cells and that at the more proximate prostate cells is reduced.

There are not only chemotherapeutic drugs for the treatment of prostate cancer, there are now also chemotherapeutic drugs for the treatment of BPH. The electrochemotherapeutic treatment method of the present invention, as exemplified in FIG. 5, makes it possible to enhance the delivery and uptake of these type of drugs into the cells of prostate, gland 514.

In the foregoing description of the present invention, it was tacitly assumed that the cells being treated by ECT were situated within the body of the patient. However, this need not be the case. In such cases as the the treatment of blood cancers, it may be desirable to temporarily remove the blood and/or other body fluids from the patient's body, or, alternatively, circulate the blood and/or other body fluids through a tube outside of the patient's body and to apply ECT to the blood cells while they are outside of the patient's body using RF, microwave, high-energy infra-red or laser electromagnetic wave energy or ultrasonic acoustic wave energy, as appropriate for this purpose. In this case, the drug or chemotherapeutic agent being used may not be systemically applied to the patient, but instead be applied to the blood and/or other body fluids while outside of the patient's body.

The present invention is suitable for use with enhancing the delivery and uptake of any type of one or more drugs or chemotherapeutic agent to specified target cells, using microwave, high-energy infra-red or laser electromagnetic wave energy or ultrasonic acoustic wave energy shocks to enhance the therapeutic delivery of such drugs into cells at one or more specified sites. This has important advantages over the use of prior-art DC shocks for this purpose. First, it is much easier to shock well defined tissue volumes with RF, microwave, high-energy infra-red or laser electromagnetic wave energy or ultrasonic acoustic wave energy than with DC, as is illustrated by the above-described applicators shown in FIGS. 2–5. This is most important when dealing with highly toxic drugs such as chemotherapeutic agents. Second, with RF, microwave, high-energy infra-red or laser electromagnetic wave energy or ultrasonic acoustic wave energy shocks one can take advantage of the resonance phenomena associated with the flux of molecules into and out of cells by choosing the appropriate frequency or frequencies to produce the shocks. Thus it should be possible to target specific types of cells at specific locations, or produce shocks specifically tailored to specific drugs.

What is claimed is:

1. In an electrochemotherapeutic treatment method comprising the steps of (1) systemically administering an agent which includes at least one of a drug agent and a chemotherapeutic agent to a patient, and (2), a short time after the systemic administration of said agent, applying force-field shock pulses to at least one site of said patient of sufficiently high-intensities to open large transient pores in plasma membranes of cells of each site to which said force-field shock pulses are applied, thereby permitting said agent to enter said cells of that site through said pores and result in locally enhanced therapeutic effect; the improvement wherein said step (2) comprises the step of:
   a) applying at least one of said force-field shock pulses that comprises a burst of high-frequency wave energy to a given site of said patient of sufficiently high-intensity to open large transient pores in plasma membranes of cells of said given site.

2. The method defined in claim 1, wherein:
said burst of high-frequency wave energy comprises high-frequency electromagnetic wave energy.

3. The method defined in claim 2, wherein:
said burst of high-frequency electromagnetic wave energy comprises radio-frequency wave energy.

4. The method defined in claim 2, wherein:
said burst of high-frequency electromagnetic wave energy comprises microwave wave energy.

5. The method defined in claim 1, wherein:
said burst of high-frequency wave energy comprises ultrasonic acoustic wave energy.

6. The method defined in claim 1, wherein said step (a) comprises the step of:
applying to said one site a train of said high-frequency wave-energy force-field shock pulses in which energy in each pulse of said train and duty cycle of said pulse train are sufficiently low to effect only a minimal rise in temperature of said cells at said given site.

7. The method defined in claim 1, wherein step (a) comprises the step of:
   b) applying to a tumor lesion at said one site at least one directed beam of said force-field shock pulses of high-frequency wave-energy bursts.

8. The method defined in claim 7, wherein step (b) comprises the step of:
   c) applying to a relatively superficially-seated tumor lesion at said one site a single directed beam of said force-field shock pulses of high-frequency wave-energy bursts.

9. The method defined in claim 7, wherein step (b) comprises the step of:
   c) simultaneously applying to a relatively deep-seated tumor lesion at said one site from different directions a plurality of separate directed beams of said force-field shock pulses of high-frequency wave-energy bursts that effectively intersect at said one site;
   wherein said plurality of separate directed beams at their intersection have a combined intensity which is sufficient to open large transient pores in the plasma membranes of cells at said one site, although the intensity of said force-field shock pulses of any single one of said separate directed beams is insufficient in itself to do so.

10. The method defined in claim 7, wherein said agent is preferentially absorbed by cells of a given type of metastasized tumors within said patient's body relative to its absorption by normal cells of said patient's body, and wherein step (b) comprises the step of:
    c) applying said force-field shock pulses of high-frequency wave-energy bursts to at least a substantial portion of said patient's whole body;
    whereby said patient's metastasized tumors of said given type are treated.

11. In an electrochemotherapeutic method for treating prostate disease of a patient comprising the steps of (1) systemically administering an agent which includes at least one of a drug agent and a chemotherapeutic agent to the patient, and (2), a short time after the systemic administration of said agent, applying sufficient squeezing pressure to non-prostate tissue which surrounds an orifice of the patient in a vicinity of the patient's prostate both to compress the prostate and non-prostate tissue and to increase a distance from a given location within said orifice to said non-prostate tissue; the improvement wherein said method comprises the further step of:
    while said pressure is being applied, irradiating said prostate through said non-prostate tissue from said given location within said orifice with a force-field shock of pulsed microwave energy of sufficiently high-intensity to open large transient pores in plasma membranes of cells of said prostate and thereby permit said agent to enter into and be taken up by said cells of said prostate through said pores, to thereby enhance a therapeutic effect of said agent on said prostate.

12. The method defined in claim 11, wherein said step comprises:
    irradiating said prostate with a force-field shock of pulsed microwave energy in which the energy in each pule of said pulsed microwave energy and the duty cycle of said pulsed microwave energy are insufficient to raise said prostate's temperature to a temperature which in itself is therapeutic.

13. The method defined in claim 11, wherein said step comprises:
    irradiating said prostate with a force-field shock of pulsed microwave energy in which the energy in each pulse of said pulsed microwave energy and the duty cycle of said pulsed microwave energy are only sufficient to effect a minimal rise in said prostate's and non-prostate's tissue temperature.

14. The method defined in claim 11, wherein:
the step of applying squeezing pressure comprises applying squeezing pressure to that non-prostate tissue which surrounds a patient's urethra thereby to increase the diameter of said urethra; and
the step of irradiating said prostate includes the step of irradiating said prostate from said urethra.

* * * * *